United States Patent [19]

Litman et al.

[11] 4,318,707

[45] Mar. 9, 1982

[54] MACROMOLECULAR FLUORESCENT QUENCHER PARTICLE IN SPECIFIC RECEPTOR ASSAYS

[75] Inventors: David J. Litman, Cupertino, Calif.; Zvi Harel, Haifa, Israel; Edwin F. Ullman, Atherton, Calif.

[73] Assignee: Syva Company, Palo Alto, Calif.

[21] Appl. No.: 156,160

[22] Filed: Jun. 3, 1980

Related U.S. Application Data

[63] Continuation-in-part of Ser. No. 964,099, Nov. 24, 1978.

[51] Int. Cl.$^3$ .................... G01N 33/54; G01N 33/58; G01N 21/76
[52] U.S. Cl. .................... 23/230 B; 23/915; 424/8; 424/12; 435/7; 435/8
[58] Field of Search .................... 424/8, 12; 23/230 B; 435/7, 8

[56] References Cited

U.S. PATENT DOCUMENTS

| 3,791,932 | 2/1974 | Schuurs | 435/7 |
|---|---|---|---|
| 3,853,987 | 12/1974 | Dreyer | 23/230 B X |
| 3,901,654 | 8/1975 | Gross | 23/230 B |
| 3,935,074 | 1/1976 | Rubenstein | 23/230 B X |
| 3,996,345 | 12/1976 | Ullman | 23/230 B X |
| 3,998,943 | 12/1976 | Ullman | 23/230 B X |
| 4,052,010 | 10/1977 | Baker | 424/12 |
| 4,059,685 | 11/1977 | Johnson | 435/7 |
| 4,067,959 | 1/1978 | Bolz | 435/7 |
| 4,104,029 | 8/1978 | Maier | 23/230 B |
| 4,134,792 | 1/1979 | Boguslaski | 435/7 |
| 4,158,135 | 6/1979 | Thorell | 250/303 |
| 4,160,645 | 7/1979 | Ullman | 23/230 B |
| 4,174,384 | 11/1979 | Ullman | 435/7 X |
| 4,193,983 | 3/1980 | Ullman | 424/8 X |
| 4,199,559 | 4/1980 | Ullman | 424/8 |
| 4,201,763 | 5/1980 | Monthony | 424/8 |
| 4,208,479 | 6/1980 | Zuk | 424/8 X |
| 4,220,450 | 9/1980 | Maggio | 424/8 X |
| 4,233,402 | 11/1980 | Maggio | 435/7 |
| 4,238,195 | 12/1980 | Boguslaski | 23/230 B |

FOREIGN PATENT DOCUMENTS 2332697  6/1973  Fed. Rep. of Germany .

OTHER PUBLICATIONS

Chemical Abstracts, 80:144347t (1974).
"Applied Biochemistry and Bioengineering", vol. 1, L. B. Wingard et al., eds., 135-138, Academic Press, New York, 1976.

*Primary Examiner*—Sidney Marantz
*Attorney, Agent, or Firm*—Bertram I. Rowland

[57] ABSTRACT

Homogeneous immunoassay employing a light absorbing particle to which a member of an immunological pair (mip)-ligand and antiligand is bound and a labeled mip, where the label is light emitting. The labeled mip becomes bound to the light absorbing particle in proportion to the amount of analyte in the assay medium. Thus, the light emitted from the medium is related to the amount of analyte in the medium.

8 Claims, No Drawings

MACROMOLECULAR FLUORESCENT QUENCHER PARTICLE IN SPECIFIC RECEPTOR ASSAYS

CROSS-REFERENCE TO RELATED APPLICATIONS

This application is a continuation-in-part of application Ser. No. 964,099, filed Nov. 24, 1978.

BACKGROUND OF THE INVENTION

1. Field of the Invention

The measurement of trace amounts of a wide variety of organic compounds has become essential in medicine, ecology, quality control, and the like. One class of methods commonly referred to as immunoassays is dependent upon the use of a compound or receptor which specifically binds to another compound having a particular spatial and polar organization. The compound and its receptor form a homologous pair, referred to as ligand and receptor, where the receptor is normally antibody. One of the members of the homologous pair is bound to a label which is capable of providing a detectible signal.

The category of immunoassays may be further broken down into what is referred to as heterogeneous and homogeneous. The heterogeneous techniques are dependent upon separating associations or complexes of the homologous pair from members of the pair which are not associated. Since the complexes will substantially differ in molecular weight from the dissociated members, techniques such as centrifugation can be used to separate the associated from the dissociated members. One can then measure the label either in the phase containing the dissociated members or the phase containing the associated members. For the most part the labels which have found use in the heterogeneous methods are radiolabels, enzymes, and fluorescent molecules.

An alternative to physical separation is to bind one of the members of the homologous pair to a solid support, which may or may not absorb the aqueous medium. The solid support can then provide for the separation since the complexed or associated ligand and receptor is bound to the solid support. This allows for relatively easy separation between the aqueous assay medium and the solid support.

The homogeneous methods rely on the formation of complexes to modulate the signal obtained from the label. The dissociated conjugated label provides for a different level of signal from the conjugated label associated with its receptor. For example, where the ligand is conjugated to a stable free radical, the association of the conjugate with its homologous receptor results in a substantial flattening of the esr peaks. With enzymes as labels to which ligands have been conjugated, the binding of receptor to the ligands can result in steric inhibition of the approach of substrate to the active site of the enzyme or allosteric modification of enzyme activity. The presence of ligand in the assay medium reduces the amount of available receptor for binding to the label conjugate and thus affects the amount of the label conjugate which becomes associated with receptor. Therefore, by measurement of the signal from the label, one can relate the level of signal to the amount of ligand in the assay medium.

An alternative to employing the receptor to directly affect the signal by its bulk is the opportunity to bring together two labels which interact. Where a ligand is polyepitopic or a polyepitopic ligand is formed from monoepitopic ligands, the opportunity exists to allow for receptors which are labeled differently to be brought together when bound to the ligand or to have ligand with one label and receptor with a different label, which when the ligand and receptor are associated bring the labels into close spatial proximity. Where the different labels interact to affect the amount of signal observed, the associated ligand and receptor will provide for a different signal level from the dissociated labeled receptor.

This technique has been employed with chromophores which are related by one of the chromophores fluorescing at a wavelength of an energy which is accepted by the other chromophore, which acts as a quencher. Also, by employing two different enzymes, where the product of one enzyme is the substrate of the other enzyme, one can observe an enhanced turnover in the complex, as compared to the dissociated label.

The focus of effort in the homogeneous immunoassay area has been directed to either employ the properties of the complex to modulate the signal or to provide for the complex to bring together in close spatial proximity different labels which are related and provide for different degrees of interaction in relation to their distance from each other.

In developing immunoassays, there are many considerations, not the least of which is sensitivity. For measuring extremely small amounts of a ligand, it is either necessary to have a label which is detected at very low levels with high accuracy or to provide for a plurality of events associated with an individual ligand. Another consideration is interference by the foreign materials present and the degree to which the interference can be minimized or removed.

Another problem associated with immunoassays is labeling, particularly where the ligand or receptor is impure. The background resulting from conjugation of the label to compounds other than those of the homologous pair must be maintained at a minimum in order to obtain a satisfactorily sensitive assay. Other considerations include simplicity of protocol, ease of measurement, reproducibility, sensitivity to extraneous factors and the like.

Description of the Prior Art

Engasser and Horvath, Applied Biochem. Bioengineering, 1, 127 (1976) Academic Press, report the kinetic and diffusion effects on the immobilization of enzymes. U.S. Pat. No. 3,817,837 describes a homogeneous enzyme immunoassay. U.S. Pat. No. 3,996,345 describes a homogeneous immunoassay employing two chromophores related by being a fluorescer and a quencher. Co-pending application Ser. No. 893,650, filed Apr. 5, 1978, now U.S. Pat. No. 4,233,402, describes a technique employing a plurality of enzymes, where the substrate of one enzyme is a product of the other enzyme. U.S. Pat. No. 4,160,645 describes a homogeneous immunoassay employing a non-enzymatic catalyst as a label. Co-pending application Ser. No. 906,514, filed May 16, 1978, now U.S. Pat. No. 4,193,983, describes a labeled liquid discontinuous phase for use in immunoassays. Application Ser. No. 667,996, filed Mar. 18, 1976, describes a homogeneous immunoassay employing as a label an enzyme substrate. See also U.S. Pat. No. 3,853,987, which discloses particles to which are conjugated radioactive and fluorescent labels and antibodies. See also U.S. Pat. No. 4,001,400.

SUMMARY OF THE INVENTION

Methods and compositions are provided for the determination of an analyte which is a member of a specific binding or immunological pair (mip)—ligand and homologous receptor—where the method is carried out without separation, employing a light absorbing particle, conveniently carbon particle, to which one of the members of the specific binding pair is bound, and mip labeled with an electronically excitable functionality, where the light emission is modified when the electronically excitable functionality capable of light emission is bound to the light absorbing particle through the binding of mips. By providing for a distribution of the electronically excitable label between the continuous liquid assay medium and the dispersed particles in relation to the amount of analyte present in the assay medium, the light emission observed or rate of change of light emission can be related to the amount of analyte in the medium.

Combinations of reagents are provided as kits to enhance the observed sensitivity of the assay by providing for ratios to substantially optimize the sensitivity for the range of interest of the analyte.

DESCRIPTION OF THE SPECIFIC EMBODIMENTS

A method is provided for determining low concentrations of organic compounds in a wide variety of media, particularly physiologically active compounds in physiological fluids. The compounds may be naturally occurring or synthetic, may be naturally present or administered. The method employs as an assay medium, a continuous liquid aqueous phase and a homogeneously dispersed solid phase comprised of discrete small particles having relatively slow settling rates and serving to modulate the light emission from molecules having functionalities in electronically excited states. These molecules for the most part will be fluorescers, but chemiluminescers and phosphors may also be employed.

The particles employed in this invention are for the most part large discrete particles which are capable of reducing the excitation intensity and/or reducing the emission intensity of electronically excitable molecules. Conveniently, carbon particles can be employed to which a member of the specific binding pair or immunological pair is bound, either covalently or non-covalently, usually non-covalently. To the degree the label which undergoes excitation to an electronically activated state is bound to a particle, the observed fluorescence will be lower. By providing for a protocol and reagents which allow for distribution of the label between the liquid assay medium and the particles in relation to the amount of analyte in the medium, the observed light emission from the medium can be related to the amount of analyte in the medium.

The analyte will be a member of a specific binding or immunological pair, hereinafter referred to as "mip". Normally, in the assay, there will be the ligand and its homologous receptor, although in certain situations, a receptor may also serve as a ligand, so that the assay will involve a ligand, its receptor and an anti-receptor (receptor for the receptor). In the assay, a mip will be bound to the particle, e.g. charcoal, and a mip will be labeled with a molecule capable of undergoing electronic excitation, either by absorption of light or through a chemical reaction, usually by absorption of light, i.e. fluorescer.

In carrying out the method, one combines the analyte containing sample, the labeled particle, the labeled mip, as well as any additional reagents and determines the light emission from the assay medium. By comparing the observed light emission with light emission obtained from an assay medium having a known amount of analyte, one can qualitatively or quantitatively determine the analyte of interest.

In performing the subject method, there will be at least two reagents, usually two reagents: the particle conjugate; and the labeled mip. By appropriate choice of these molecules, one can perform assays under a wide variety of conditions and tailor the assays to varying availabilities of the mips.

DEFINITIONS

Analyte—the compound or composition to be measured, which may be a ligand, which is mono-, or polyepitopic, antigenic or haptenic, a single or plurality of compounds which share at least one common epitopic site or a receptor.

Mip—member of an immunological pair or specific binding pair, where one member of the pair has an area on the surface or in a cavity which specifically binds to a particular spatial and polar organization of the other member of the pair. The mips are referred to as ligand and receptor (antiligand).

Ligand—any organic compound for which a receptor naturally exists or can be prepared.

Receptor (antiligand)—any compound or composition capable of recognizing a particular spatial and polar organization of a molecule i.e. epitopic or determinant site. Illustrative receptors include naturally occurring receptors, e.g. thyroxine binding globulin, antibodies, enzymes, Fab fragments, lectins and the like.

Ligand Analog—a modified ligand which can compete with the analogous ligand for a receptor, the modification providing means to join a ligand analog to another molecule. The ligand analog will normally differ from the ligand by more than replacement of a hydrogen with a bond which links the ligand analog to a hub or label.

Particle—the particle is of a different phase than the bulk aqueous phase of the assay medium and is a discrete, stable, particulate material that absorbs light of the excitation wavelengths and/or emission wavelengths of the signal label. The particles will be readily dispersible in an aqueous medium. When a mip is bound to a particle, either covalently or non-covalently, the resulting product will be referred to as a "particle conjugate."

Signal label—the signal label will be conjugated to a mip to provide the signal label conjugate. The signal label is a molecule which provides an electronically excited functionality capable of light emission, which may gain its electronic excitation, either physically, by absorption of light, or chemically, by undergoing a reaction which results in electronic excitation of the molecule. When the signal label is bound to a mip, usually covalently, the resulting product will be referred to as a "signal label conjugate."

METHOD

The subject assay is carried out in an aqueous zone at a moderate pH, generally close to optimum assay sensitivity, without separation of the assay components or products. The assay zone for the determination of analyte is prepared by employing an appropriate aqueous medium, normally buffered, the unknown sample, which may have been subject to prior treatment, the particle conjugate, the signal label conjugate, all of the materials required for the signal producing system for producing a detectible signal, as well as members of the specific binding pair of their analogs, as required.

The presence of ligand or its homologous receptor (antiligand) in the unknown will affect the partition of the signal label conjugate between the particle and the bulk solution in the assay medium.

In carrying out the assay, an aqueous medium will normally be employed. Other polar solvents may also be included, usually oxygenated organic solvents of from 1–6, more usually from 1–4 carbon atoms, including alcohols, ethers and the like. Usually these cosolvents will be present in less than about 40 weight percent, more usually in less than about 20 weight percent.

The pH for the medium will usually be in the range of about 4–11, more usually in the range of about 5–10, and preferably in the range of about 6.5–9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the assay and usually constant temperatures during the period of the measurement, particularly for rate determinations. The temperatures for the determination will generally range from about 10°–50° C., more usually from about 15°–40° C.

The concentration of analyte which may be assayed will generally vary from about $10^{-4}$ to $10^{-15}$M, more usually from about $10^{-6}$ to $10^{-13}$M. Considerations such as whether the assay is qualitative, semi-quantitative or quantitative, the particular detection technique and the concentration of the analyte of interest will normally determine the concentration of the other reagents.

While the concentrations of the various reagents in the assay medium will generally be determined by the concentration range of interest of the analyte, the final concentration of each of the reagents will normally be determined empirically to optimize the sensitivity of the assay over the range of interest. The total binding sites of the members of the specific binding pair which are reciprocal to the analyte will be not less than about 0.1 times the minimum concentration of interest based on binding sites of analyte and usually not more than about 1,000 times the maximum concentration of interest based on analyte binding sites, usually about 0.1 to 100 times, more usually about 0.3–10 times the maximum concentration of interest. By concentration is intended the available concentration, that is, the concentration at saturation, and not necessarily the actual concentration where members of the specific binding pair may not be equally available for binding.

The ratio of the particle conjugate to the signal label conjugate will vary widely depending upon the members involved, their nature, and the particular protocol. For example, if antibody is the analyte, one could have large excesses of ligand on the particle with a limited amount of signal label-ligand conjugate which would bind to the particle in proportion to the amount of antiligand in the medium. Where antiligand is bound to the particle and a competition is provided between signal label-ligand conjugate and ligand analyte, the ratio of signal label-ligand conjugate and antiligand would be optimized for maximum sensitivity in the range of interest of ligand.

The order of addition of the various reagents may vary widely, depending upon the particular conjugates, the nature of the conjugates, the nature of the analyte, and the relative concentrations of the analyte and reagents. Also affecting the order of addition is whether an equilibrium mode or rate mode is employed in the determination.

Since with many receptors, the association of the mips is almost irreversible during the time period of the assay, one will normally avoid combining the particle conjugate with the signal label conjugate, prior to the addition of the analyte, where the two conjugates are reciprocal or homologous mips. By contrast, where the two conjugates have the same mips, one could combine them prior to introduction of the unknown sample into the assay medium. Regardless of the nature of the analyte, all the reagents can be added simultaneously and either a rate or equilibrium determination made.

One or more incubation steps may be involved in preparing the assay medium. For example, it may be desirable to incubate an antigen analyte with labeled receptor. In addition, it may be desirable to have a second incubation after addition of the particle conjugate. Whether to employ an incubation period and the length of the incubation period, will depend to a substantial degree on the mode of determination—rate or equilibrium—and the rate of binding of the receptor to the ligand. Usually, incubation steps will vary from about 0.5 min to 6 hrs, more usually from about 5 min to 1 hr. Incubation temperatures will generally range from about 4° to 50° C., more usually from about 15° to 37° C.

The temperature at which the signal is observed will generally range from about 10° to 50° C., more usually from about 15° to 40° C.

Standard assay media can be prepared which have known amounts of the analyte. The observed signal for the standard assay media may then be plotted, so as to relate concentration to signal. Once a standard curve has been established, a signal may be directly related to the concentration of the analyte.

The time for measuring the signal will vary depending on whether a rate or equilibrium mode is used, the sensitivity required, the nature of the signal producing system and the like. For a rate mode the times between readings will generally vary from about 5 sec to 6 hrs, usually about 10 sec to 1 hr. For the equilibrium mode, after a steady state is achieved, a single reading may be sufficient or two readings over any convenient time interval may suffice.

The ligand may be mono- or polyepitopic. In most situations this difference will not affect the manner in which the assay is performed. Where the analyte is a ligand, the mip in the particle conjugate may be either ligand or receptor. The signal label conjugate can have either ligand or receptor. However, where both the particle conjugate and the signal label conjugate have receptor, the ligand must be polyepitopic or made so by employing a poly(ligand analog) as an additional reagent. That is, a sandwich technique is employed where the ligand binds to the particle conjugate and provides epitopic sites for binding of the signal label conjugate to the particle conjugate.

Where the receptor is the analyte, the particle conjugate and the signal label conjugate may have the same or different mip, with the proviso that receptor is polyvalent when ligand is involved in both conjugates.

In the event that the analyte and the two conjugates all have or contain the same mip, then the homologous member must be added and it must be provided in polyepitopic form, either as an antibody, or a polyvalent receptor, where it is a receptor, or as polyhapten (poly(ligand analog)), where it is a ligand.

MATERIALS

The components employed in the assay will be the particle conjugate, the signal label conjugate and the reagents which are the remaining members of the signal producing system, as well as the analyte, and, as appropriate, poly(ligand analog), and polyvalent receptor. Employed in the preparation of the reagents, will be the particle, the signal label, capable of electronic excitation, normally a fluorescer, and as appropriate mips.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations or assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usualy range from about 5,000 to 60,000 molecular weight.

A large number of ligands and linking groups employed with ligand analogs, which linking groups are also applicable for linking to receptors, are set forth in the parent application Ser. No. 964,099 on pages 23 to 42, all of which is incorporated herein by reference.

Signal Producing System

The signal producing system involves formation of an electronically excited molecules capable of emitting light. The electronic excitation can be achieved either by the intermolecular energy transfer to or the absorption of light by a molecule which results in the raising of an electron from one orbital to an orbital of higher energy or, in a chemiluminescent compound, as a result of a chemical reaction, either catalyzed or uncatalyzed, which raises an electron to a higher orbital. In view of the greater simplicity of the fluorescent system, the fluorescent system will be preferred.

Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthene, 7-hydroxycoumarin, phenoxazine, salicylate, strophanthidin, porphyrins, triarylmethanes and flavin.

Individual fluorescent compounds which have functionalities for linking or can be modified to incorporate such functionalities include dansyl chloride, fluoresceins such as 3,6-dihydroxy-9-phenylxanthhydrol, rhodamineisothiocyanate, N-phenyl 1-amino-8-sulfonatonaphthalene, N-phenyl 2-amino-6-sulfonatonaphthalene, 4-acetamido-4-isothiocyanatostilbene-2,2'-disulfonic acid, pyrene-3-sulfonic acid, 2-toluidinonaphthalene-6-sulfonate, N-phenyl, N-methyl 2-amino-naphthalene-6-sulfonate, ethidium bromide, atebrine, auromine-0, 2-(9'-anthroyl)palmitate, dansyl phosphatidylethanolamine, N,N'-dioctadecyl oxacarbocyanine, N,N'-dihexyl oxacarbocyanine, merocyanine, 4-(3'-pyrenyl)butyrate, d-3-aminodesoxyequilenin, 12-(9'-anthroyl)stearate, 2-methylanthracene, 9-vinylanthracene, 2,2'-(vinylene-p-phenylene)bis-benzoxazole, p-bis[2-(4-methyl-5-phenyloxazolyl)]benzene, 6-dimethylamino-1,2-benzophenazin, retinol, bis(3'-aminopyridinium) 1,10-decandiyl diiodide, sulfonaphthyl hydrazone of hellebrigenin, chlortetracycline, N-(7-dimethylamino-4-methyl-2-oxo-3-chromenyl) maleimide, N-[p-(2-benzimidazoyl)-phenyl] maleimide, N-(4-fluoranthyl) maleimide, bis(homovanillic acid), resazurin, 4-chloro-7-nitro-2.1.3-benzooxadiazole, merocyanine 540, resorufin, rose bengal, and 2,4-diphenyl-3(2H)-furanone.

Where samples are involved having endogenous fluorescence, it will normally be desirable to have a fluorescer absorbing light above the light absorbed by the endogenous fluorescers. This will usually require a fluorescer absorbing light above about 350 nm, preferably above about 400 nm, more preferably above about 450 nm.

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

A diverse number of families of compounds have been found to provide chemiluminescence under a variety of conditions. One family of compounds is 2,3-dihydro-1,-4-phthalazinedione. The most popular compound is luminol, which is the 5-amino compound. Other members of the family include the 5-amino-6,7,8-trimethoxy- and the dimethylamino-[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl, active esters e.g. p-nitrophenyl and a peroxide e.g. hydrogen peroxide, under basic conditions. Alternatively, luciferins may be used in conjunction with luciferase or lucigenins.

Particle Conjugate

Depending upon the nature of the particle, the mip may be bound covalently or non-covalently. In many instances, non-covalent binding will suffice. Therefore, the particle conjugate for the most part will have the mip non-covalently bound.

Many different types of particles may be employed for modulating the light emission while remaining substantially uniformly dispersed in the assay medium during the assay. Of particular interest are carbon particles, such as charcoal, lamp black, graphite, colloidal carbon and the like.

Besides carbon particles metal sols may also find use, particularly of the noble metals, gold, silver, and platinum. Other metal derived particles may include metal sulfides, such as lead, silver or copper sulfides or metal oxides, such as iron or copper oxide.

Dyes may be employed bound to polymeric particles e.g. latex particles or may involve water insoluble organic dyes, such as rubrene and phthalocyanines.

The particle conjugate can be prepared by combining an aqueous solution containing the mip in an appropriately buffered solution, generally at a pH in the range of about 4 to 10 and allowing the mixture to stand for an extended period of time, usually at a temperature in the range of from 0° to 30° C. Times may range from several minutes to 12 days, more usually from about 1 hr to 6 days. Depending upon the size of the original particles, the particles to which the mip has been absorbed may be reduced in size by mechanical means, conveniently sonication.

The particles will generally be of a size in the range of about 10 nm to 100μ, more usually about 500 nm to 25μ.

If desired, the particles may be chemically modified to provide for reactive functionalities which will covalently bond the mip to the particle. However, for the purposes of this invention, this will normally not be necessary, and therefore adsorption will be relied upon for the particle conjugate.

Signal Label Conjugate

The signal label conjugate will have a signal label, covalently or non-covalently, usually covalently bound to a mip-ligand or antiligand. Normally, the signal label is a small compound, generally under 1,000 molecular weight, which has functionalities or can be functionalized for bonding to the mip.

Normally, there will be on the average at least one signal label per mip. With large mips the number of signal labels will usually be less than about one per 2,000 daltons, usually less than about one per 5,000 daltons. The number of signal labels will be governed by such considerations as their physical and chemical effects on the mip, e.g. solubility, conformation, and determinant sites, as well as intermolecular effects e.g. quenching between fluorescent molecules. Usually, with mips having molecular weights in the range of about 20,000 to 300,000 daltons there will be on the average about 1 to 60 signal labels per molecule, more usually about 2 to 50 signal labels per molecule.

The particular linking group is not significant. A wide variety of linking groups are known and may be employed as indicated for use with ligand analogs.

Ancillary Materials

Where only fluorescer is involved, no specific ancillary materials will be required. Where chemiluminescers are involved, the other materials which are required will depend upon whether the chemiluminescence is enzymatically catalyzed or uncatalyzed. Where enzyme catalysis is involved, in addition to the enzyme, substrates, cofactors or the like may be required. Where the chemiluminescence is uncatalyzed by enzyme, oxidants, e.g. peroxides, or the like will frequently be required. The various compositions for providing chemiluminescence have already been described, and it would be these compositions which would be included.

Kits

As a matter of convenience, the reagents can be provided as kits, where the reagents are in predetermined ratios, so as to substantially optimize the sensitivity of the assay in the range of interest. After any required reconstitution of the reagents, the particle conjugate will normally be dispersed in an aqueous medium having a density and viscosity such that the particles remain substantially uniformly dispersed over the time period in which the assay is to be run, usually greater than 30 min. By employing high density additives or adjusting the density of the particles, the desired density relationship can be achieved. Viscosity can be increased by the addition of hydroxylic additives e.g. sucrose, glycerol, dextran and the like.

For the subject kits employing a fluorescer label, there will be required the particle conjugate and the fluorescer label conjugate. The two reagents may be combined, where the mips are the same and may or may not be in separate containers where the mips are homologous.

EXPERIMENTAL

The following examples are offered by way of illustration and not by way of limitation.

(All percents and parts not otherwise indicated are by weight, except for mixtures of liquids which are by volume. All temperatures not otherwise idicated are centigrade. The following abbreviations are employed: HIgG-human gamma-globulin; antiHIgG-antibodies to human gamma-globulin; PBS-phosphate buffered saline; BSA-bovine serum albumin.

EXAMPLE 1—Absorption of anti-HIgG to Carbon Black

Two parallel runs were performed; one employing Monarch 1300 carbon black (GP-2664, 13 nm particle size); and the other Sterling R (V5373, 75 nm particle size), both from Cabot Corportion. (Carbon black consists of aggregates created by the fusing of smaller particles (12–100 nm). The size of the aggregates is in the 1–12μ range. Particle size relates to the surface area of the aggregates.) Each of the carbon blacks (50 mg) was introduced into separate reaction vessels, followed by the addition of 0.5 ml of anti-HIgG solution, PBS, pH 7.8 (40.3 mg/ml protein, 20% specific antibody) containing 25 $\mu l^{14}C$ sheep IgG, followed by the addition of 1.5 ml PBS, pH 7.8 and the reaction mixture was stirred at room temperature for three days. At the end of this time, the solutions were sonicated with a Bronson microtip for 15 min, 2.5 power, 50% pulse. (It was later found that sonication is optional.) The solution was then centrifuged and 1 ml of the supernatant was employed for $^{14}C$ counting. The supernatant was then diluted with 4 ml of PBS containing 0.2 mg/ml BSA, the mixture spun, and 1 ml of the supernatant counted. The process was repeated three times. The precipitate was resuspended in 4.0 ml PBS plus 0.2 mg/ml BSA, pH 7.8. The following table indicates the results.

TABLE 1

| | $^{14}$C counting* | |
|---|---|---|
| | Monarch | Sterling |
| 1st sup | 370** | 26,881*** |
| 2nd sup | 67 | 685 |
| 3rd sup | 52 | 190 |
| 4th sup | 50 | 92 |
| 5th sup |  | 80 |

*0.5ml antiHIgG (20mg) soln. 86,229cpm added to 2.0ml reaction mixture; counted 1ml of the supernatant; background 35cpm.
**99% of $^{14}$C spun down, 20mg bound.
***38% of $^{14}$C spun down, 4.6mg bound.

Based on the above results, with the Monarch carbon black, it is calculated that 19.9 mg of protein bound to 50 mg carbon.

In order to demonstrate the subject invention, a number of assays were carried out. Employed in these assays is a fluorescein-HIgG conjugate prepared as described in U.S. Pat. No. 4,174,384, having an F/P ratio (fluorescer/protein mole ratio) of approximately 16.2. The solution of fluorescein-HIgG conjugate (F-HIgG) had 0.82 mg/ml protein of which 20 μl was dissolved in 0.344 ml of a PBS pH 7.2 solution containing 10 Mg ovalbumin/ml and 0.496 ml PBS, pH 7.8. The particle conjugate was diluted 1:12 by dissolving 41.7 μl of the particle conjugate in 200 μl of the above ovalbumin-PBS solution and 258 μl of the above PBS solution. The assay was performed by combining 20 μl of the HIgG solution of the appropriate concentration, 250 μl of PBS, 20 μl of the particle conjugate solution followed by an additional 250 μl of PBS. After standing for 0.25 hr, 20 μl of the F-HIgG solution, ($3 \times 10^{-9}$M final concentration) and 250 μl of PBS was added and the mixture allowed to stand for 1 hr. The O.D$_{520}$ of the particle conjugate was 0.561, 1 cm path length. The series was repeated where 10 μl of sheep serum was added to provide for a final solution containing 1.3% sheep serum. The following table indicates the results.

TABLE 2

| HIgG* | % Fluorenscence | |
|---|---|---|
| M | w/o serum | 1.3% serum |
|  | 100** | 100** |
| $1 \times 10^{-7}$ | 77.5; 77.9 | 72.1; 72.4 |
| $3.3 \times 10^{-8}$ | 75.6; 76.9 |  |
| $1 \times 10^{-8}$ | 70.7; 71.8 |  |
| $3 \times 10^{-9}$ | 65.7; 64.9 | 62.8; 63.6 |
| $1 \times 10^{-9}$ | 56.3; 56.5 |  |
| $3 \times 10^{-10}$ | 50.4; 50.5 |  |
| neg. | 41.1; 43.0 | 47.8; 48.4 |
| neg.sup. | 52.5; 52.8 |  |

*F-HIgG $3 \times 10^{-9}$M; neg - no HIgG added; neg.sup - assay sample centrifuged to determine total amount of fluorescer binding to charcoal by measuring supernatant
**Fluorescence in absence of charcoal particles corrected for charcoal absorbance It is evident from the above results that a sensitive accurate assay is available by using light absorbent particles with a fluorescer label. The binding of the fluorescer-mip conjugate to the carbon particle through the intermediacy of the specific binding of the immunological pair provides for a broad dynamic range for the determination of analytes, where relatively simple stable reagents can be employed, which are easily prepared and can be readily characterized. The protocol is simple and a wide variety of available equipment can be employed in the subject assay.

Although the foregoing invention has been described in some detail by way of illustration and example for purposes of clarity of understanding, it will be obvious that certain changes and modifications may be practiced within the scope of the appended claims.

What is claimed is:

1. An assay method for determining the presence in a sample of an analyte which is a mip, wherein said mip is a member of a specific binding pair consisting of ligand and its homologous antiligand;
    said method employing:
    (a) a continuous aqueous medium;
    (b) a particle conjugate comprising a mip bound to a light absorbing particle;
    (c) a signal label conjugate, comprising a signal label conjugated to a mip, wherein said signal label is a fluorescer of chemiluminescer;
    wherein the amount of signal label conjugate bound to said particle conjugate is related to the amount of analyte in said aqueous medium;
    said method comprising:
    combining in an aqueous medium,
    (a) said sample;
    (b) said particle conjugate substantially uniformly dispersed in said medium;
    (c) said signal label conjugate;
    (d) the homologous member of said specific binding pair, where the analyte, particle conjugate, and signal label conjugate are the same member of said specific binding pair; and
    (e) when the label is excited by chemical activation, additional reagents necessary for the production of chemiluminescence; and
    determining the amount of light emission from said assay medium containing both bound and unbound signal label conjugate as compared to an assay medium having a known amount of analyte.

2. The method according to claim 1, wherein said signal label is a fluorescer, said light absorbing particle is carbon and said aqueous assay medium is at a temperature in the range of about 10° to 50° C. and at a pH in the range of about 5 to 10.

3. A method according to claims 1 or 2, wherein said analyte is a protein.

4. A method according to claims 1 or 2, wherein said particle conjugate has antiligand as said mip.

5. A method according to claims 1 or 2, wherein said fluorescer absorbs light at a wavelength greater than about 350 nm.

6. A method according to claim 3, wherein said particle conjugate has antiligand as said mip.

7. A method according to claim 3, wherein said fluorescer absorbs light at a wavelength greater than about 350 nm.

8. A method according to claim 6, wherein said fluorescer absorbs light at a wavelength greater than about 350 nm.

* * * * *

UNITED STATES PATENT AND TRADEMARK OFFICE
CERTIFICATE OF CORRECTION

PATENT NO. : 4,318,707
DATED : March 9, 1982
INVENTOR(S) : David J. Litman et al.

It is certified that error appears in the above—identified patent and that said Letters Patent is hereby corrected as shown below:

Column 11, line 23, change "Mg" to --mg--.

Column 11, line 41, change "Fluorenscence" to --Fluorescence--.

Column 12, line 19, change "of" to --or--.

Signed and Sealed this

Twenty-fifth Day of May 1982

[SEAL]

Attest:

GERALD J. MOSSINGHOFF

Attesting Officer    Commissioner of Patents and Trademarks